(12) United States Patent
Brophy et al.

(10) Patent No.: US 8,124,579 B2
(45) Date of Patent: Feb. 28, 2012

(54) HEAT SHOCK PROTEIN 20-RELATED POLYPEPTIDES AND USES THEREFOR

(75) Inventors: Colleen Brophy, Tempe, AZ (US);
Elizabeth Furnish, Tempe, AZ (US);
Padmini Komalavilas, Tempe, AZ (US);
Catherin Dreiza, Phoenix, AZ (US);
Alyssa Panitch, W Lafayette, IN (US)

(73) Assignee: Arizona Board of Regents, Tempe, AZ (US)

( * ) Notice: Subject to any disclaimer, the term of this patent is extended or adjusted under 35 U.S.C. 154(b) by 1092 days.

(21) Appl. No.: 10/575,294

(22) PCT Filed: Oct. 15, 2004

(86) PCT No.: PCT/US2004/034989
§ 371 (c)(1),
(2), (4) Date: Oct. 5, 2007

(87) PCT Pub. No.: WO2005/037236
PCT Pub. Date: Apr. 28, 2005

(65) Prior Publication Data
US 2008/0132443 A1  Jun. 5, 2008

Related U.S. Application Data

(60) Provisional application No. 60/512,211, filed on Oct. 17, 2003, provisional application No. 60/530,306, filed on Dec. 16, 2003.

(51) Int. Cl.
*A61K 38/16* (2006.01)
(52) U.S. Cl. ...... 514/1.1; 514/21.2; 514/21.3; 514/21.8; 530/324; 530/325; 530/329; 530/350
(58) Field of Classification Search ............... None
See application file for complete search history.

(56) References Cited

U.S. PATENT DOCUMENTS

| | | | |
|---|---|---|---|
| 7,135,453 B2 | 11/2006 | Brophy et al. | |
| 7,381,699 B2 | 6/2008 | Brophy et al. | |
| 2003/0060399 A1 | 3/2003 | Brophy et al. | |
| 2003/0190364 A1 | 10/2003 | Panitch et al. | |
| 2010/0009903 A1 | 1/2010 | Brophy et al. | |

FOREIGN PATENT DOCUMENTS

| | | |
|---|---|---|
| JP | 2001/278894 | 10/2001 |
| WO | WO 03/018758 A1 | 3/2003 |
| WO | WO 2003-018758 | 3/2003 |
| WO | WO 2004-017912 | 3/2004 |
| WO | WO 2004-075914 | 9/2004 |
| WO | WO 2005/037236 | 4/2005 |

OTHER PUBLICATIONS

S Fawell et al., Proc Natl Acad Sci USA 91: 664-668,1994.
Maurice Green et al., Cell 55 : 1179-1188, 1988.
Alan D. Frankel et al., Cell 55 : 1189-1193, 1988.
Steven R. Schwarze et al., Science 285 : 1569-1572,1999.
Mudit Tyagi et al., J Biol Chem 276 : 3254-3261,2001.
Alan Ho et al., Cancer Res 61: 474-477,2001.
G. J. Ramakers, W. H. Moolenaar, Exp. Cell Res. 245,252 (1998).
A. Beall et al., J. Biol. Chem. 274 (16),11344 (1999).
C. R. Flynn et al., Faseb J. 17, 1358 (2003).
C. S. Heacock, J. R. Bamburg, Anal. Biochem. 135,22 (1983).
J. E. Murphy-Ullrich, S. Gurusiddappa, W. A. Frazier, M. Hook, J. Biol. Chem. 268, 26784 (1993).
J. E. Murphy-Ullrich et al., J. Cell. Sci. 109,2499 (1996).
R. Niwa, K. Nagata-Ohashi, M. Takeichi, K. Mizuno, T. Uemura, Cell 108,233 (2002).
A. Gohla, G. M. Bokoch, Curr. Biol. 12(19), 1704 (2002).
H. Fu, R. R. Subramanian, S. C. Masters, Annu. Rev. P7zarmacol. Toxicol. 40,617 (2000).
M. B. Yaffe et al., Cell 91, 961 (1997).
S. H. Zhang, R. Kobayashi, P. R. Graves, H. Piwnica-Worms, and N. K. Tonks, J Biol. Chem. 272, 27281 (1997).
M. P. Washbum, D. Wolters, J. R. Yates III, Nat. Biotechnol. 19,242 (2001).
S. D. Macomson, C. M. Brophy, W. Miller, V. A. Harris, E. G. Shaver, Neurosurgery 51,204 (2002).
Birkenfeld J et al., Biochem J. 369(Pt1): 45-54 (2003).
Jens Pfannstiel et al., J. Biol. Chem. 276(52): 49476-49484 (2001).
Ghosh M. et al., Science 304: 743-746 (2004).
Bertling E et al., Mol. Biol. Cell 15: 2324-2334 (2004).
Wilker E. et al., J. Mol. Cell Cardiol. 37(3): 633-642 (2004).
Eibert SM et al., Proc Natl Acad Sci USA 101(7): 1957-1962 (2004).
Paavilainen VO et al., J. Biol. Chem. 277(45): 43089-43095 (2002).
Shen YH et al., Mol Biol. Cell 14: 4721-4733 (2003).
Morris MC et al., J. Biol. Chem. 275(37): 28849-28857 (2000).
Rembold et al., J. Appl. Physiol 91:1460-1466 (2001).
Wang et al., Diabetes 50:1821-1827.
Beall et al., J. Biol Chem. 272(17): 11283-11297 (1997).
Brophy et al., J. Biol Chem., 274(10): 6324-6329 (1999).
Kanefusa Kato et al., J. Biol. Chem.. 269(21): pp. 15302-15309 (1994).
Dreiza Catherine et al., FASEB J. express article 10.1096/fj.04-2911fje. Published online Dec. 14, 2004.
Tessier, et al., "The Small Heat Shock Protein (HSP) 20 is Dynamically Associated with the Actin Cross-Linking Protein Actinin", 2003, Journal of Surgical Research, vol. 111, pp. 152-157.
Parmiter, et al., "Protein Transduction of Biomimetic Peptides Leads to Changes in the Actin Cytoskeleton of 3T3 Cells", 2003, FASEB Journal, vol. 17, Abstract No. 599.6.
Brophy, et al., "The Small Heat Shock-Related Protein-20 is an Actin-Axxociated Protein", 1999, Journal of Vascular Surgery, vol. 29, pp. 326-333.
Supplementary European Search Report—EP04796051, Date of Completion of the Search Jun. 26, 2009.
Database WPI Week 200212, Thomson Scientific, London, GB, AN2002-085935.
International Search Report and Written Opinion—(PCT/US2004/034989) Date of Mailing Oct. 19, 2005.
International Search Report and Written Opinion—(PCT/US2004/004999) Date of Mailing Jul. 22, 2004.

*Primary Examiner* — Anish Gupta
(74) *Attorney, Agent, or Firm* — McCarter & English, LLP; Steven Davis

(57) ABSTRACT

The present invention provides novel HSP20-based polypeptides and pharmaceutical compositions thereof, and methods for using such polypeptides and pharmaceutical compositions for various therapeutic uses.

2 Claims, 2 Drawing Sheets

HSP20 associates with 14-3-3

IP cofilin probed for 14-3-3
IP 14-3-3 probed for HSP20

Lane 1: Control no treatment

Lane 2: 1μM forskolin (5 min)

Lane 3: 1μM 5-HT (5 min), 1μM forskolin (5 min). Forskolin raises cAMP levels leading to the phosphorylation of HSP20 and association with 14-3-3

HEAT SHOCK PROTEIN 20-RELATED POLYPEPTIDES AND USES THEREFOR

CROSS REFERENCE

This application claims priority from U.S. Provisional Patent Application Ser. Nos. 60/512,211 filed Oct. 17, 2003 and 60/530,306 filed Dec. 16, 2003, the disclosures of which are incorporated by reference herein in their entirety.

STATEMENT OF GOVERNMENT FUNDING

This invention was made with government support under Grant Number RO1 HL58027-01 awarded by the National Institute of Health. The government has certain rights in the invention.

FIELD OF INVENTION

The invention is in the fields of cell and molecular biology, polypeptides, drug discovery, and therapeutic methods of use.

BACKGROUND OF THE INVENTION

Cellular processes such as cell adhesion, cytolinesis, cell motility, migration, and muscular contraction/relaxation require dynamic reorganization of the actin cytoskeleton. Activation of cyclic nucleotide signaling pathways in various cell types leads to profound alterations in the cytoskeleton, which include loss of central stress fibers and focal adhesion plaques; cytoplasmic retraction with the formation of thin processes; and rounding of the cell bodies (1). In aggregate, these changes lead to a star-shaped appearance that has been termed "stellation."

The cyclic nucleotide signaling pathways include adenylate cyclase/cAMP/cAMP-dependent protein kinase (PKA) and guanylate cyclase/cGMP/cGMP-dependent protein kinase (PKG). These pathways converge at the phosphorylation of the small heat shock-related protein, HSP20 on serine 16 (2, 3).

We have previously demonstrated that HSP20 and certain peptides derived therefrom show promise as therapeutic agents for the following: (a) inhibiting smooth muscle cell proliferation and/or migration; (b) promoting smooth muscle relaxation; (c) increasing the contractile rate in heart muscle; (d) increasing the rate of heart muscle relaxation; (e) promoting wound healing; (f) reducing scar formation; (g) disrupting focal adhesions; (h) regulating actin polymerization; and (i) treating or inhibiting one or more of intimal hyperplasia, stenosis, restenosis, atherosclerosis, smooth muscle cell tumors, smooth muscle spasm, angina, Prinzmetal's angina (coronary vasospasm), ischemia, stroke, bradycardia, hypertension, pulmonary (lung) hypertension, asthma (bronchospasm), toxemia of pregnancy, pre-term labor and/or delivery, pre-eclampsia/eclampsia, intrauterine growth restriction, Raynaud's disease or phenomenon, hemolytic-uremia, non-occlusive mesenteric ischemia, anal fissure, achalasia, sexual dysfunction, migraine, ischemic muscle injury associated with smooth muscle spasm, vasculopathy, such as transplant vasculopathy, bradyarryhmia, bradycardia, congestive heart failure, stunned myocardium, pulmonary hypertension, and diastolic dysfunction. (See, for example, US 20030060399 filed Mar. 27, 2003; WO2004017912 published Mar. 4, 2004) However, these applications did not demonstrate that the activities of HSP20 result from specific protein-protein interactions with other molecules within the cell. The identification of specific proteins that HSP20 interacts with to carry out its cellular functions could lead to the design of improved HSP20-derived therapeutics.

SUMMARY OF THE INVENTION

In one aspect, the present invention provides a composition comprising a polypeptide consisting of a sequence according to general formula I:

X1-X2-X3 wherein X1 and X3 are independently absent or comprise a transduction domain; and
wherein X2 is $[Z1-Z2-RRA-Z3-AP]_u$, wherein
Z1 is absent or is W;
Z2 is absent or is L
Z3 is selected from the group consisting of S, T, Y, D, E, phosphoserine analogs and phosphotyrosine analogs; and
u is 1-2, wherein when u is 2, the two copies of X2 are optionally separated by a spacer.

In another aspect, the present invention provides pharmaceutical compositions, comprising one or more polypeptides of the present invention and a pharmaceutically acceptable carrier.

In another aspect, the present invention provides isolated nucleic acid sequences encoding a polypeptide of the present invention. In further aspects, the present invention provides recombinant expression vectors comprising the nucleic acid sequences of the present invention, and host cells transfected with the recombinant expression vectors of the present invention.

In another aspect, the invention provides improved biomedical devices, wherein the biomedical devices comprise one or more polypeptides of the present invention disposed on or in the biomedical device. In various embodiments, such biomedical devices include stents, grafts, shunts, stent grafts, angioplasty devices, balloon catheters, fistulas, wound dressings, and any implantable drug delivery device.

In a further aspect, the present invention provides methods for one or more of the following therapeutic uses
(a) inhibiting smooth muscle cell proliferation and/or migration; (b) promoting smooth muscle relaxation; (c) increasing the contractile rate in heart muscle; (d) increasing the rate of heart muscle relaxation; (e) promoting wound healing; (f) reducing scar formation; (g) disrupting focal adhesions; (h) regulating actin polymerization; and (i) treating or inhibiting one or more of intimal hyperplasia, stenosis, restenosis, atherosclerosis, smooth muscle cell tumors, smooth muscle spasm, angina, Prinzmetal's angina (coronary vasospasm), ischemia, stroke, bradycardia, hypertension, pulmonary (lung) hypertension, asthma (bronchospasm), toxemia of pregnancy, pre-term labor and/or delivery, pre-eclampsia/eclampsia, intrauterine growth restriction, Raynaud's disease or phenomenon, hemolytic-uremia, non-occlusive mesenteric ischemia, anal fissure, achalasia, male or female sexual dysfunction, migraine, ischemic muscle injury associated with smooth muscle spasm, vasculopathy, such as transplant vasculopathy, bradyarrythmia, bradycardia, congestive heart failure, stunned myocardium, pulmonary hypertension, and diastolic dysfunction;
wherein the method comprises administering to a subject in need thereof an effective amount to carry out the one or more therapeutic uses of one or more polypeptides according to the present invention, or functional equivalents thereof.

DETAILED DESCRIPTION OF THE INVENTION

Figure 1:
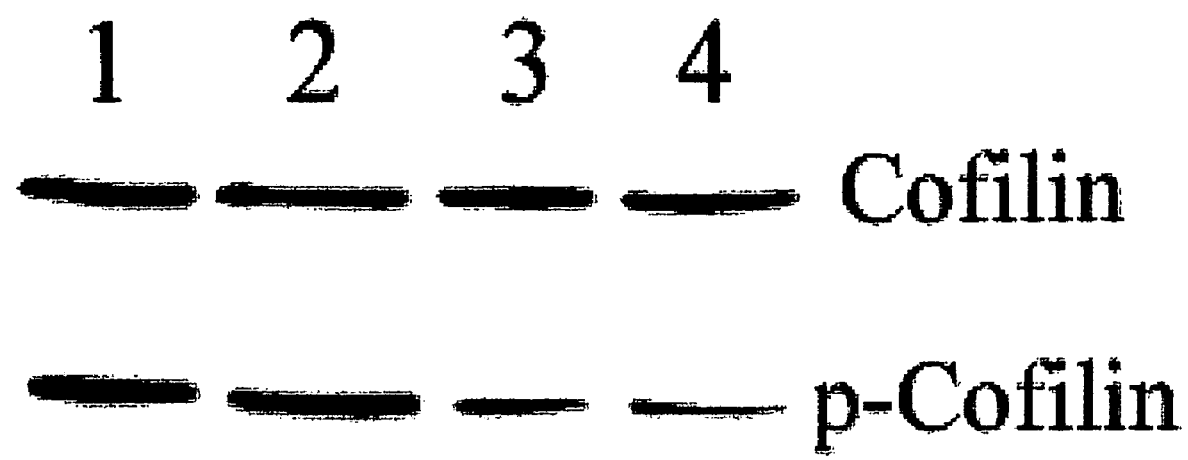
FIG. 1: PhosphoHSP20 peptide decreases phospho-cofilin levels. 3T3 cells were either untreated (lane 1) or treated with 10 μM LPA (lane 2), 10 μM FSK (lane 3), or 25 μM FITC-pHSP20 (lane 4) for 30 min at 37° C. Cell lysates (25 μg/lane) were analyzed by SDS-PAGE and probed with antibodies against cofilin (upper) or phospho-cofilin (lower). These blots are representative of 3 independent experiments.

Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), and *Gene Transfer and Expression Protocols*, pp. 109-128, ed. E. J. Murray, The Humana Press Inc., Clifton, N.J.)

The single letter designation for amino acids is used predominately herein. As is well known by one of skill in the art, such single letter designations are as follows:

A is alanine; C is cysteine; D is aspartic acid; E is glutamic acid; F is phenylalanine; G is glycine; H is histidine; I is isoleucine; K is lysine; L is leucine; M is methionine; N is asparagine; P is proline; Q is gluatamine; R is arginine; S is serine; T is threonine; V is valine; W is tryptophan; and Y is tyrosine.

As used herein, the singular forms "a", "an" and "the" include plural referents unless the context clearly dictates otherwise. For example, reference to a "polypeptide" means one or more polypeptides.

As discussed in US 20030060399 filed Mar. 27, 2003; WO2004017912 published Mar. 4, 2004), HSP20, and certain peptides derived therefrom, show promise as therapeutic agents for each of the following: (a) inhibiting smooth muscle cell proliferation and/or migration; (b) promoting smooth muscle relaxation; (c) increasing the contractile rate in heart muscle; (d) increasing the rate of heart muscle relaxation; (e) promoting wound healing; (f) reducing scar formation; (g) disrupting focal adhesions; (h) regulating actin polymerization; and (i) treating or inhibiting one or more of intimal hyperplasia, stenosis, restenosis, atherosclerosis, smooth muscle cell tumors, smooth muscle spasm, angina, Prinzmetal's angina (coronary vasospasm), ischemia, stroke, bradycardia, hypertension, pulmonary (lung) hypertension, asthma (bronchospasm), toxemia of pregnancy, pre-term labor and/or delivery, pre-eclampsia/eclampsia, Raynaud's disease or phenomenon, hemolytic-uremia, non-occlusive mesenteric ischemia, anal fissure, achalasia, impotence, migraine, ischemic muscle injury associated with smooth muscle spasm, vasculopathy, such as transplant vasculopathy, bradyarrythmia, bradycardia, congestive heart failure, stunned myocardium, pulmonary hypertension, and diastolic dysfunction The present invention provides evidence that the HSP20 peptides may achieve these therapeutic effects by binding to the 14-3-3 protein and interfering with its ability to bind to cofilin. As discussed herein, proteins of the ADF (actin depolymerizing family)/cofilin family are involved in actin turnover via the regulation of polymerization/depolymerization. In particular, phosphorylated cofilin is inactive; however, when dephosphorylated by the slingshot family of phosphatases, cofilin catalyzes the depolymerization of actin (8). Phosphorylated cofilin is stabilized by binding to 14-3-3 proteins (9). The 14-3-3 proteins are thought to be general biochemical regulators because they are involved with many cellular functions and have a broad range of ligands, such as receptors, kinases, phosphatases, and docking molecules (10). In addition to playing a structural role by stabilizing the activity and conformation of signaling proteins, 14-3-3 proteins also act as scaffolding proteins by interacting with and localizing phosphorlyated motifs (11). The domain surrounding the phosphorylation site in HSP20 contains a sequence (RRApSAP) (SEQ ID NO:54) similar to a putative 14-3-3 binding motif (RSXpSXP) (SEQ ID NO:55). Previous results have shown that, although highly favored, the presence of nonphosphoryated serine immediately following R is not required in this motif (12). Thus, one plausible mechanism by which pHSP20 leads to actin disruption is via competitive binding to 14-3-3 proteins resulting in release and dephosphorylation of cofilin. Consistent with this hypothesis, treatment with forskolin or with pHSP20 led to decreases in the amount of phosphorylated cofilin (FIG. 3). A similar decrease in phosphorylated cofilin has been observed with hep I treatment (13).

Taken together, these data suggest that short sequences or motifs surrounding a phosphorylation site can have profound effects on cellular biology. Since these peptides have little or no predicted tertiary structure (15), these peptide motifs are likely altering cellular function through changes in protein-protein interactions. In the case of phosphorylated HSP20, these data suggest that the motif surrounding the phosphorylation site binds to 14-3-3 proteins. Since the binding to 14-3-3 proteins is noncovalent, competitive dissociation of cofilin from 14-3-3 proteins by phosphorylated HSP20 could lead to dephosphorylation and activation of cofilin as an actin depolymerizing protein.

While not being bound by a specific mechanism of action, it is our hypothesis that the HSP20 (or HSP20 polypeptide) effects discussed above result from a similar competitive dissociation of cofilin from 14-3-3 proteins by HSP20. Thus, the polypeptides of the invention are expected to be at least as effective as HSP20 or peptides derived therefrom (as disclosed in, for example US 20030060399 filed Mar. 27, 2003), while being less expensive to produce and more specific for the interaction with 14-3-3 rather than interactions between other sites on the HSP20 protein with additional intracellular proteins, thus leading to fewer potential non-desired interactions with other biological components, and therefore fewer side effects.

Therefore, in one aspect, the present invention provides a composition comprising a polypeptide consisting of an amino acid sequence according to general formula I:

X1-X2-X3 wherein X1 and X3 are independently absent or comprise a transduction domain; and
wherein X2 is $[Z1-Z2-RRA—Z3-AP]_u$, wherein
Z1 is absent or is W;
Z2 is absent or is L;
Z3 is selected from the group consisting of S, T, Y, D, E, phosphoserine analogs and phosphotyrosine analogs; and
u is 1-2, wherein when u is 2, the two copies of X2 are optionally separated by a spacer.

In this aspect, u can be one or two, as 14-3-3 binding in some case is over thirty times more effective when two binding sites are present on its binding partner, presumably due to 14-3-3 dimerization (See, for example, Yaffe et al, *Cell*, 91: 961-971, 1997.)

In certain embodiments, Z1 and/or Z2 are present. While not being bound by a specific mechanism, it is believed that the presence of one or both of these residues in the polypeptides of the invention may serve to interact with hydrophobic regions in the 14-3-3 "binding pocket," and thus may serve to increase specificity and affinity of interactions with 14-3-3.

The term "polypeptide" is used in its broadest sense to refer to a sequence of subunit amino acids, amino acid analogs, or peptidominetics. The subunits are linked by peptide bonds, except where noted. The polypeptides described herein may be chemically synthesized or recombinantly expressed. Preferably, the polypeptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with the standard deprotecting, neutralization, coupling and wash protocols of the original solid phase procedure of Merrifield (1963, *J. Am. Chem. Soc.* 85: 2149-2154), or the base-labile Nα-amino protected 9-fluorenylmethoxycarbonyl (Fmoc) amino acids first described by Carpino and Han (1972, *J. Org. Chem.* 37: 3403-3409). Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, for example, in Stewart and Young, 1984, Solid Phase Synthesis, Second Edition, Pierce Chemical Co., Rockford, Ill.; Fields and Noble, 1990, *Int. J. Pept. Protein Res.* 35: 161-214, or using automated synthesizers. The polypeptides of the invention may comprise D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare peptides with novel properties. For example, a peptide may be generated that incorporates a reduced peptide bond, i.e., $R_1$—$CH_2$—$NH$—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

According to various embodiments of the polypeptides of the invention, Z3 is S, T, Y, D E, a phosphoserine mimic, or a phosphotyrosine mimic. It is more preferred that Z3 is S, T, or Y; more preferred that Z3 is S or T, and most preferred that Z3 is S. In these embodiments where Z3 is S, T, or Y, it is most preferred that Z3 is phosphorylated. When Z3 is D or E, these residues have a negative charge that mimics the phosphorylated state. The polypeptides of the invention are optimally effective in the methods of the invention when Z3 is phosphorylated, is a phosphoserine or phosphotyrosine mimic, or is another mimic of a phosphorylated amino acid residue, such as a D or E residue. Examples of phosphoserine mimics include, but are not limited to, sulfoserine, amino acid mimics containing a methylene substitution for the phosphate oxygen, 4-phosphono(difluoromethyl)phenylanaline, and L-2-amino-4-(phosphono)-4,4-difuorobutanoic acid. Other phosphoserine mimics can be made by those of skill in the art; for example, see Otaka et al., *Tetrahedron Letters* 36: 927-930 (1995). Examples of phosphotyrosine mimics include, but are not limited to, phosphonomethylphenylalanine, difluorophosphonomethylphenylalanine, fluoro-O-malonyltyrosine and O-malonyltyrosine. (See, for example, Akamatsu. et. al., *Bioorg Med Chem* Jan. 5, 1997 (1): 157-63).

In embodiments where the Z3 residue is phosphorylated, the peptide can be synthesized using a phosphorylated amino acid (or phospho-mimic) during polypeptide synthesis, or the Z3 residue can be phosphorylated after its addition to the polypeptide chain.

Thus, according to these various aspects, a representative sample of polypeptides according to general formula I include, but are not limited to the following:

| | |
|---|---|
| RRASAP | (SEQ ID NO: 1) |
| LRRASAP | (SEQ ID NO: 2) |
| WLRRASAP | (SEQ ID NO: 3) |
| RRATAP | (SEQ ID NO: 4) |
| LRRATAP | (SEQ ID NO: 5) |
| WLRRATAP | (SEQ ID NO: 6) |
| RRAYAP | (SEQ ID NO: 7) |
| LRRAYAP | (SEQ ID NO: 8) |
| WLRRAYAP | (SEQ ID NO: 9) |
| RRADAP | (SEQ ID NO: 10) |
| LRRADAP | (SEQ ID NO: 11) |
| WLRRADAP | (SEQ ID NO: 12) |
| RRAEAP | (SEQ ID NO: 13) |
| LRRAEAP | (SEQ ID NO: 14) |
| WLRRAEAP | (SEQ ID NO: 15) |
| RRASAPRRASAP | (SEQ ID NO: 16) |
| LRRASAPLRRASAP | (SEQ ID NO: 17) |
| WLRRASAPWLRRASAP | (SEQ ID NO: 18) |
| RRATAPRRATAP | (SEQ ID NO: 19) |
| LRRATAPLRRATAP | (SEQ ID NO: 20) |
| WLRRATAPWLRRATAP | (SEQ ID NO: 21) |
| RRAYAPRRAYAP | (SEQ ID NO: 22) |
| LRRAYAPLRRAYAP | (SEQ ID NO 23) |
| WLRRAYAPWLRRAYAP | (SEQ ID NO: 24) |
| RRADAPRRADAP | (SEQ ID NO: 25) |
| LRRADAPLRRADAP | (SEQ ID NO: 26) |
| WLRRADAPWLRRADAP | (SEQ ID NO: 27) |
| RRAEAPRRAEAP | (SEQ ID NO: 28) |

```
LRRAEAPLRRAEAP            (SEQ ID NO: 29)

WLRRAEAPWLRRAEAP          (SEQ ID NO: 30)
```

Other specific polypeptides falling within the scope of general formula I will be readily apparent to one of skill in the art based on the teachings herein.

In a further embodiment, the polypeptides of the present invention consist of a combination of different sequences from the region [Z1-Z2-RRA-Z3-AP]$_u$. In this embodiment, for example, the polypeptide can consist of 1 copy of SEQ ID NO:9 and 1 copy of SEQ ID NO:25. In a different example, the polypeptide could consist of 1 copy of SEQ ID NO:4 and 1 copy of SEQ ID NO:20. Non-limiting examples of such polypeptides include RRASAPWLRRASAP (SEQ ID NO:31) and WLRRASAPRRASAP (SEQ ID NO:32). It will be apparent to one of skill in the art that many such combinations are possible based on the teachings of the present invention.

As used herein, the term "spacer" refers to a molecule that separates the two copies of X2 to provide more optimal spacing for use of the polypeptides in the methods of the invention. The spacers preferably provide between 17-50 Å between copies of X2 (based on optimal spacing between 14-3-3 binding peptides (Yaffe et al, Cell, 91: 961-971, 1997)). Spacers can be amino acid sequences such as GGAP or other sequences that do not adversely affect peptide solubility. In addition, short synthetic sequences such as hydrophilic oligomers (e.g., poly(ethylene glycol), poly(vinyl alcohol) and poly(propylene oxide)), can be used as spacers with heterobifunctional crosslinkers. In a preferred embodiment, the spacer is a 30 Å-long flexible six-aminohexanoic acid loop spacer (Yaffe et al, Cell, 91: 961-971, 1997).

In a preferred embodiment, at least one of X1 and X3 comprises a transduction domain. As used herein, the term "transduction domain" means one or more amino acid sequence or any other molecule that can carry the active domain across cell membranes. These domains can be linked to other polypeptides to direct movement of the linked polypeptide across cell membranes. In some cases the transducing molecules do not need to be covalently linked to the active polypeptide. In a preferred embodiment, the transduction domain is linked to the rest of the polypeptide via peptide bonding. (See, for example, Cell 55: 1179-1188, 1988; Cell 55: 1189-1193, 1988; Proc Natl Acad Sci USA 91: 664-668, 1994; Science 285: 1569-1572, 1999; J Biol Chem. 276: 3254-3261, 2001; and Cancer Res 61: 474-477, 2001) In this embodiment, any of the polypeptides as described above would include at least one transduction domain. In a further embodiment, both X1 and X3 comprise transduction domains. In a further preferred embodiment, the transduction domain(s) is/are selected from the group consisting of (R)$_{4-9}$ (SEQ ID NO:33); GRKKRRQRRRPPQ (SEQ ID NO:34); AYARAAARQARA (SEQ ID NO:35); DAATATRGRSAASRPTERPRAPARSASRPRRPVE (SEQ ID NO:36); GWTLNSAGYLLGLINLKALAALAKKIL (SEQ ID NO:37); PLSSISRIGDP (SEQ ID NO:38); AAVALLPAVLLALLAP (SEQ ID NO:39); AAVLLPVLLAAP (SEQ ID NO:40); VTVLALGALAGVGVG (SEQ ID NO:41); GALFLGWLGAAGSTMGAWSQP (SEQ ID NO:42); GWTLNSAGYLLGLINLKALAALAKKIL (SEQ ID NO:43); KLALKLALKALKAALKLA (SEQ ID NO:44); KETWWETWWTEWSQPKKKRKV (SEQ ID NO:45); KAFAKLAARLYRKAGC (SEQ ID NO:46); KAFAKLAARLYRAAGC (SEQ ID NO:47); AAFAKLAARLYRKAGC (SEQ ID NO:48); KAFAALAARLYRKAGC (SEQ ID NO:49); KAFAKLAAQLYRKAGC (SEQ ID NO:50), AGGGGYGRKKRRQRRR (SEQ ID NO:51); YGRKKRRQRRR (SEQ ID NO:52); and YARAAARQARA (SEQ ID 53).

In another aspect, the present invention provides pharmaceutical compositions, comprising one or more of the polypeptides disclosed herein, and a pharmaceutically acceptable carrier. Such pharmaceutical compositions are especially useful for carrying out the methods of the invention described below.

For administration, the polypeptides are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art. The polypeptides may be linked to other compounds to promote an increased half-life in vivo, such as polyethylene glycol. Such linkage can be covalent or non-covalent as is understood by those of skill in the art.

The polypeptides or pharmaceutical compositions thereof may be administered by any suitable route, including orally, parentarally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Preferred embodiments for administration vary with respect to the condition being treated.

The polypeptides may be made up in a solid form (including granules, powders or suppositories) or in a liquid form (e.g., solutions, suspensions, or emulsions). The polypeptides of the invention may be applied in a variety of solutions. Suitable solutions for use in accordance with the invention are sterile, dissolve sufficient amounts of the polypeptides, and are not harmful for the proposed application.

In another aspect, the present invention provides an isolated nucleic acid sequence encoding a polypeptide of the present invention. Appropriate nucleic acid sequences according to this aspect of the invention will be apparent to one of skill in the art based on the disclosure provided herein and the general level of skill in the art.

In another aspect, the present invention provides an expression vector comprising DNA control sequences operably linked to the isolated nucleic acid molecules of the present invention, as disclosed above. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites.

Such expression vectors can be of any type known in the art, including but not limited to plasmid and viral-based expression vectors.

In a further aspect, the present invention provides genetically engineered host cells comprising the expression vectors of the invention. Such host cells can be prokaryotic cells or eukaryotic cells, and can be either transiently or stably transfected, or can be transduced with viral vectors.

In another aspect, the invention provides improved biomedical devices, wherein the biomedical devices comprise one or more of the polypeptides of the present invention disposed on or in the biomedical device. In a preferred embodiment, the one or more polypeptides are phosphorylated, as discussed above.

As used herein, a "biomedical device" refers to a device to be implanted into a subject, for example, a human being, in order to bring about a desired result. Particularly preferred biomedical devices according to this aspect of the invention include, but are not limited to, stents, grafts, shunts, stent grafts, fistulas, angioplasty devices, balloon catheters, implantable drug delivery devices, wound dressings such as films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), cellophane, and biological polymers.

As used herein, the term "grafts" refers to both natural and prosthetic grafts and implants. In a most preferred embodiment, the graft is a vascular graft.

As used herein, the term "stent" includes the stent itself, as well as any sleeve or other component that may be used to facilitate stent placement.

As used herein, "disposed on or in" means that the one or more polypeptides can be either directly or indirectly in contact with an outer surface, an inner surface, or embedded within the biomedical device. "Direct" contact refers to disposition of the polypeptides directly on or in the device, including but not limited to soaking a biomedical device in a solution containing the one or more polypeptides, spin coating or spraying a solution containing the one or more polypeptides onto the device, implanting any device that would deliver the polypeptide, and administering the polypeptide through a catheter directly on to the surface or into any organ.

"Indirect" contact means that the one or more polypeptides do not directly contact the biomedical device. For example, the one or more polypeptides may be disposed in a matrix, such as a gel matrix or a viscous fluid, which is disposed on the biomedical device. Such matrices can be prepared to, for example, modify the binding and release properties of the one or more polypeptides as required.

In another aspect, the invention provides methods for the use of a composition comprising a polypeptide consisting of an amino acid sequence according to general formula II

X1-X2-X3 wherein X1 and X3 are independently absent or comprise a transduction domain; and
wherein X2 is $[Z1\text{-}Z2\text{-}R\text{—}Z4\text{-}A\text{—}Z3\text{-}AP]_u$, wherein
Z1 is absent or is W;
Z2 is absent or is L;
Z3 is selected from the group consisting of S, T, Y, D, E, phosphoserine analogs and phosphotyrosine analogs;
Z4 is R or S; and
u is 1-2, wherein when u is 2, the two copies of X2 are optionally separated by a spacer, or functional equivalents thereof;

for the preparation of a medicament for carrying out one or more of the following therapeutic uses:

(a) inhibiting smooth muscle cell proliferation and/or migration;
(b) promoting smooth muscle relaxation;
(c) increasing the contractile rate in heart muscle;
(d) increasing the rate of heart muscle relaxation;
(e) promoting wound healing;
(f) reducing scar formation;
(g) disrupting focal adhesions;
(h) regulating actin polymerization; and
(i) treating or inhibiting one or more of intimal hyperplasia, stenosis, restenosis, atherosclerosis, smooth muscle cell tumors, smooth muscle spasm, angina, Prinzmetal's angina, ischemia, stroke, bradycardia, hypertension, pulmonary hypertension, asthma, toxemia of pregnancy, pre-term labor and/or delivery, pre-eclampsia/eclampsia, intrauterine growth restriction, Raynaud's disease or phenomenon, hemolytic-uremia, non-occlusive mesenteric ischemia, anal fissure, achalasia, sexual dysfunction, migraine, ischemic muscle injury associated with smooth muscle spasm, vasculopathy, bradyarrythmia, congestive heart failure, stunned myocardium, and diastolic dysfunction.

In this aspect, X1, X3, Z1, Z2, Z3, and u are as described above. In a preferred embodiment of the methods of the invention, Z4 is R. In a further preferred embodiment of all of the methods of the present invention, the one or more polypeptides are phosphorylated, as disclosed above.

In a preferred embodiment, the therapeutic is administered to a mammal; in a more preferred embodiment, the mammal is a human.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

As used herein, the term "inhibit" or "inhibiting" means to limit the disorder in individuals at risk of developing the disorder.

As used herein, "administering" includes in vivo administration, as well as administration directly to tissue ex vivo, such as vein grafts.

Intimal hyperplasia is a complex process that leads to graft failure, and is the most common cause of failure of arterial bypass grafts. While incompletely understood, intimal hyperplasia is mediated by a sequence of events that include endothelial cell injury and subsequent vascular smooth muscle proliferation and migration from the media to the intima. This process is associated with a phenotypic modulation of the smooth muscle cells from a contractile to a synthetic phenotype. The "synthetic" smooth muscle cells secrete extracellular matrix proteins, which leads to pathologic narrowing of the vessel lumen leading to graft stenoses and ultimately graft failure. Such endothelial cell injury and subsequent smooth muscle cell proliferation and migration into the intima also characterize restenosis, most commonly after angioplasty to clear an obstructed blood vessel.

In some embodiments of the methods of the invention, such as those relating to inhibiting smooth muscle cell proliferation and/or migration, or promoting smooth muscle relaxation, the administering may be direct, by contacting a blood vessel in a subject being treated with one or more polypeptides of the invention. For example, a liquid preparation of one or more polypeptides according to the invention can be forced through a porous catheter, or otherwise injected through a catheter to the injured site, or a gel or viscous liquid containing the one or more polypeptides according to the invention can be spread on the injured site. In these embodiment of direct delivery, it is most preferred that the one or more polypeptides according to the invention be delivered into smooth muscle cells at the site of injury or intervention. This can be accomplished, for example, by delivering the recombinant expression vectors (most preferably a viral vector, such as an adenoviral vector) of the invention to the site. More preferably, delivery into smooth muscle cells is accomplished by using the one or more polypeptides according to the invention that include at least one transduction domain to facilitate entry into the smooth muscle cells.

In various other preferred embodiments of this methods of the invention, particularly those that involve inhibiting smooth muscle cell proliferation and/or migration, the method is performed on a subject who has undergone, is undergoing, or will undergo a procedure selected from the group consisting of angioplasty, vascular stent placement, endarterectomy, atherectomy, bypass surgery (such as coronary artery bypass surgery; peripheral vascular bypass surgeries), vascular grafting, organ transplant, prosthetic device implanting, microvascular reconstructions, plastic surgical flap construction, and catheter emplacement.

HSP20, and certain polypeptides derived therefrom, have been shown to disrupt actin stress fiber formation and adhesion plaques, each of which have been implicated in intimal hyperplasia (see US 20030060399 filed Mar. 27, 2003). The data further demonstrate a direct inhibitory effect of the HSP20 polypeptides on intimal hyperplasia (see US 20030060399 filed Mar. 27, 2003). Thus, in another embodiment, the methods comprise treating or inhibiting one or more disorder selected from the group consisting of intimal hyperplasia, stenosis, restenosis, and atherosclerosis, comprising contacting a subject in need thereof with an amount effective to treat or inhibit intimal hyperplasia, stenosis, restenosis, and/or atherosclerosis of one or more polypeptides according to the invention.

In a further embodiment of this aspect of the invention, the method is used to treat smooth muscle cell tumors. In a preferred embodiment, the tumor is a leiomyosarcoma, which is defined as a malignant neoplasm that arises from muscle. Since leiomyosarcomas can arise from the walls of both small and large blood vessels, they can occur anywhere in the body, but peritoneal, uterine, and gastro-intestinal (particularly esophageal) leiomyosarcomas are more common. Alternatively, the smooth muscle tumor can be a leiomyoma, a non-malignant smooth muscle neoplasm. In a further embodiment, the method can be combined with other treatments for smooth muscle cell tumors, such as chemotherapy, radiation therapy, and surgery to remove the tumor.

In a further embodiment, the methods of the invention are used for treating or preventing smooth muscle spasm, comprising contacting a subject or graft in need thereof with an amount effective to inhibit smooth muscle spasm of one or more polypeptides according to the invention.

It has been shown that HSP20, and certain peptides derived therefrom, are effective at inhibiting smooth muscle spasm, such as vasospasm, and may exert their anti-smooth muscle spasm effect by promoting smooth muscle vasorelaxation and inhibiting contraction (see US 20030060399 filed Mar. 27, 2003).

Smooth muscles are found in the walls of blood vessels, airways, the gastrointestinal tract, and the genitourinary tract. Pathologic tonic contraction of smooth muscle constitutes spasm. Many pathological conditions are associated with spasm of vascular smooth muscle ("vasospasm"), the smooth muscle that lines blood vessels. This can cause symptoms such as angina and ischemia (if a heart artery is involved), or stroke as in the case of subarachnoid hemorrhage-induced vasospasm if a brain vessel is involved. Hypertension (high blood pressure) is caused by excessive vasoconstriction, as well as thickening, of the vessel wall, particularly in the smaller vessels of the circulation.

Thus, in a further embodiment of the methods of the invention, the muscle cell spasm comprises a vasospasm, and the method is used to treat or inhibit vasospasm. Preferred embodiments of the method include, but are not limited to, methods to treat or inhibit angina, coronary vasospasm, Prinzmetal's angina (episodic focal spasm of an epicardial coronary artery), ischemia, stroke, bradycardia, and hypertension.

In another embodiment of the methods of the invention, smooth muscle spasm is inhibited by treatment of a graft, such as a vein or arterial graft, with the one or more polypeptides according to the invention. One of the ideal conduits for peripheral vascular and coronary reconstruction is the greater saphenous vein. However, the surgical manipulation during harvest of the conduit often leads to vasospasm. The exact etiology of vasospasm is complex and most likely multifactorial. Most investigations have suggested that vasospasm is either due to enhanced constriction or impaired relaxation of the vascular smooth muscle in the media of the vein. Numerous vasoconstricting agents such as endothelin-1 and thromboxane are increased during surgery and result in vascular smooth muscle contraction. Other vasoconstrictors such as norepinephrine, 5-hydroxytryptamine, acetylcholine, histamine, angiotensin II, and phenylephrine have been implicated in vein graft spasm. Papaverine is a smooth muscle vasodilator that has been used. In circumstances where spasm occurs even in the presence of papaverine, surgeons use intraluminal mechanical distension to break the spasm. This leads to injury to the vein graft wall and subsequent intimal hyperplasia. Intimal hyperplasia is the leading cause of graft failure.

Thus, in this embodiment, the graft can be contacted with the one or more polypeptides according to the invention, during harvest from the graft donor, subsequent to harvest (before implantation), and/or during implantation into the graft recipient (ie: ex vitro or in vivo). This can be accomplished, for example, by delivering the recombinant expression vectors (most preferably a viral vector, such as an adenoviral vector) of the invention to the site, and transfecting the smooth muscle cells. More preferably, delivery into smooth muscle is accomplished by using the one or more polypeptides according to the invention that include at least one transduction domain to facilitate entry into the smooth muscle cells. During graft implantation, it is preferred that the subject receiving be treated systemically with heparin, as heparin has been shown to bind to protein transduction domains and prevent them from transducing into cells. This approach will lead to localized protein transduction of the graft alone, and not into peripheral tissues. The methods of this embodiment of the invention inhibit vein graft spasm during harvest and/or implantation of the graft, and thus improve both short and long term graft success.

In various other embodiments of the methods of the invention, the muscle cell spasm is associated with a disorder including, but not limited to pulmonary (lung) hypertension, asthma (bronchospasm), toxemia of pregnancy, pre-term labor and/or delivery, pre-eclampsia/eclampsia, Raynaud's disease or phenomenon, hemolytic-uremia, non-occlusive mesenteric ischemia (ischemia of the intestines that is caused by inadequate blood flow to the intestines), anal fissure (which is caused by persistent spasm of the internal anal sphincter), achalasia (which is caused by persistent spasm of the lower esophageal sphincter), male or female sexual dysfunction (which is caused by a lack of relaxation of the vessels in the penis or clitoris, as erection requires vasodilation of the corpra cavemosal (penile or vaginal) blood vessels); migraine (which is caused by spasm of the intracranial blood vessels), ischemic muscle injury associated with smooth muscle spasm, and vasculopathy, such as transplant vasculopathy (a reaction in the transplanted vessels which is similar to atherosclerosis, it involves constrictive remodeling and ultimately obliteration of the transplanted blood vessels, this is the leading cause of heart transplant failure).

Preferred routes of delivery for these various indications of the different embodiments of the methods of the invention vary. Topical administration is preferred for methods involving treatment or inhibition of vein graft spasm, intimal hyperplasia, restenosis, prosthetic graft failure due to intimal hyperplasia, stent, stent graft failure due to intimal hyperplasia/constrictive remodeling, microvascular graft failure due to vasospasm, transplant vasculopathy, and male and female sexual dysfunction. As used herein, "topical administration" refers to delivering the polypeptide onto the surface of the organ.

Intrathecal administration, defined as delivering the polypeptide into the cerebrospinal fluid is the preferred route of delivery for treating or inhibiting stroke and subarachnoid hemorrhage induced vasospasm. Intraperitoneal administration, defined as delivering the polypeptide into the peritoneal cavity, is the preferred route of delivery for treating or inhibiting non-occlusive mesenteric ischemia. Oral administration is the preferred route of delivery for treating or inhibiting achalasia. Intravenous administration is the preferred route of delivery for treating or inhibiting hypertension and bradycardia. Administration via suppository is preferred for treating or inhibiting anal fissure. Aerosol delivery is preferred for treating or inhibiting asthma (ie: bronchospasm). Intrauterine administration is preferred for treating or inhibiting pre-term labor and/or delivery, pre-eclampsia/eclampsia, and intrauterine growth restriction.

In another embodiment of the methods of the invention, the methods are used to increase the contractile rate in heart muscle. Individuals that can benefit from such treatment include those who exhibit a reduced heart rate relative to either a normal heart rate for the individual, or relative to a "normal" heart rate for a similarly situated individual. As used herein, the phrase "increasing the contractile rate in heart muscle" means any increase in contractile rate that provides a therapeutic benefit to the patient. Such a therapeutic benefit can be achieved, for example, by increasing the contractile rate to make it closer to a normal contractile rate for the individual, a normal contractile rate for a similarly situated individual, or some other desired target contractile rate. In a preferred embodiment, the methods result in an increase of at least 5% in the contractile rate of the patient in need of such treatment. In further preferred embodiments, the methods of the invention result in an increase of at least 10%, 15%, 20%, 25%, 30%, 35%, 40%, 45%, and/or 50% in the contractile rate of the patient in need of such treatment. In a preferred embodiment, increasing the contractile rate in heart muscle is accomplished by increasing the heart muscle relaxation rate (ie: if the muscles relax faster they beat faster). In a more preferred embodiment, the methods of the invention result in an increase of at least 5% in the heart muscle relaxation rate of the patient in need of such treatment. In further preferred embodiments, the methods of the invention result in an increase of at least 10%, 15%, 20%, 25%, 30%, 35%, 40%, 45%, and/or 50% in the heart muscle relaxation rate of the patient in need of such treatment.

In a further embodiment of the methods of the invention, the methods are performed to treat one or more cardiac disorders that can benefit from increasing the contractile rate in heart muscle. Such cardiac disorders include bradyarrhythmias, bradycardias congestive heart failure, pulmonary hypertension, stunned myocardium, and diastolic dysfunction. As used herein, "bradyarrythmia" means an abnormal decrease of the rate of the heartbeat to less than 60 beats per minute, generally cased by a disturbance in the electrical impulses to the heart. A common cause of bradyarrythmias is coronary heart disease, which leads to the formation of atheromas that limit the flow of blood to the cardiac tissue, and thus the cardiac tissue becomes damaged. Bradyarrythmias due to coronary artery disease occur more frequently after myocardial infarction. Symptoms include, but are not limited to, loss of energy, weakness, syncope, and hypotension.

As used herein, "Congestive heart failure" means an inability of the heart to pump adequate supplies of blood throughout the body. Such heart failure can be due to a variety of conditions or disorders, including but not limited to hypertension, anemia, hyperthyroidism, heart valve defects including but not limited to aortic stenosis, aortic insufficiency, and tricuspid insufficiency; congenital heart defects including but not limited to coarctation of the aorta, septal defects, pulmonary stenosis, and tetralogy of Fallot; arrythmias, myocardial infarction, cardiomyopathy, pulmonary hypertension, and lung disease including but not limited to chronic bronchitis and emphysema. Symptoms of congestive heart failure include, but are not limited to, fatigue, breathing difficulty, pulmonary edema, and swelling of the ankles and legs.

As used herein, "Stunned myocardium" means heart muscle that is not functioning (pumping/beating) due to cardiac ischemia (lack of blood flow/oxygen to the vessels supplying the heat muscle).

As used herein, "Diastolic dysfunction" means an inability of the heart to fill with blood during diastole (the resting phase of heart contraction). This condition usually occurs in the setting of left ventricular hypertrophy. The heart muscle becomes enlarged and stiff such that it cannot fill adequately. Diastolic dysfunction can result in heart failure and inadequate heart function.

As used herein, "Pulmonary hypertension" means a disorder in which the blood pressure in the arteries supplying the lungs is abnormally high. Causes include, but are not limited to, inadequate supply of oxygen to the lungs, such as in chronic bronchitis and emphysema; pulmonary embolism, and intestinal pulmonary fibrosis. Symptoms and signs of pulmonary hypertension are often subtle and nonspecific. In the later stages, pulmonary hypertension leads to right heart failure that is associated with liver enlargement, enlargement of veins in the neck and generalized edema.

In a further embodiment of the methods of the invention, the methods are used for treating a heart muscle disorder comprising administering to an individual suffering from one or more of bradyarrythmia, bradycardia, congestive heart failure, stunned myocardium, pulmonary hypertension, and diastolic dysfunction, an amount effective to increase heart muscle contractile rate of one or more polypeptides according to the present invention.

Treating bradyarrythmia includes one or more of the following (a) improving the rate of the heartbeat to closer to normal levels for the individual, closer to a desired rate, or increasing to at least above 60 beats per minute; (b) preventing the occurrence of one or more of loss of energy, weakness, syncope, and hypotension in patients suffering from bradyaryythmia; (c) inhibiting worsening of one or more of loss of energy, weakness, syncope, and hypotension in patients suffering from bradyarrythmia and its symptoms; (d) limiting or preventing recurrence of bradyarrythmia in patients that previously suffered from bradyarrythmia; and (e) limiting or preventing recurrence of one or more of loss of energy, weakness, syncope, and hypotension in patients that previously suffered from bradyarrythmia.

Similarly, treating congestive heart failure includes one or more of the following (a) improving the heart's ability to pump adequate supplies of blood throughout the body to closer to normal levels for the individual, or closer to a desired pumping capacity; (b) limiting or preventing development of one or more of fatigue, breathing difficulty, pulmonary edema, and swelling of the ankles and legs in patients suffering from congestive heart failure; (c) inhibiting worsening of one or more of fatigue, breathing difficulty, pulmonary edema, and swelling of the ankles and legs in patients suffering from congestive heart failure and its symptoms; (d) limiting or preventing recurrence of congestive heart failure in patients that previously suffered from congestive heart failure; and (e) limiting or preventing recurrence of one or more of fatigue, breathing difficulty, pulmonary edema, and swelling of the ankles and legs in patients that previously suffered from congestive heart failure.

Treating stunned myocardium means one or more of (a) improving the ability of the heart muscle to pump by improving the oxygenation of the ischemic muscle, or by decreasing the need of the myocardial cells for oxygen and (b) limiting or preventing recurrence of stunned myocardium in patients that previously suffered from stunned myocardium.

Similarly, treating diastolic dysfunction includes one or more of (a) limiting or preventing heart failure and/or inadequate heart function by allowing the heart to relax and fill more completely; (b) limiting or preventing recurrence of diastolic dysfunction in patients that previously suffered from diastolic dysfunction; and (c) limiting or preventing recurrence of heart failure and/or inadequate heart function in patients that previously suffered from diastolic dysfunction.

Treating pulmonary hypertension includes one or more of the following (a) decreasing blood pressure in the arteries supplying the lungs to closer to normal levels for the individual, or closer to a desired pressure; (b) limiting or preventing the occurrence of one or more of enlargement of veins in the neck, enlargement of the liver, and generalized edema in patients suffering from pulmonary hypertension; (c) inhibiting worsening of one or more of enlargement of veins in the neck, enlargement of the liver, and generalized edema in patients suffering from pulmonary hypertension and its symptoms; (d) limiting or preventing recurrence of pulmonary hypertension in patients that previously suffered from pulmonary hypertension; and (e) limiting or preventing recurrence of one or more of enlargement of veins in the neck, enlargement of the liver, and generalized edema in patients that previously suffered from pulmonary hypertension.

In a further aspect, the present invention provides methods for preventing a heart muscle disorder comprising administering to an individual at risk of developing bradyarrythmia, bradycardia, congestive heart failure, stunned myocardium, pulmonary hypertension, and diastolic dysfunction an amount effective to increase heart muscle contractile rate of one or more polypeptides according to the present invention.

For example, methods to prevent congestive heart failure involve administration of one or more polypeptides according to the present invention to a subject that suffers from one or more of hypertension, anemia, hyperthyroidism, heart valve defects including but not limited to aortic stenosis, aortic insufficiency, and tricuspid insufficiency; congenital heart defects including but not limited to coarctation of the aorta, septal defects, pulmonary stenosis, and tetralogy of Fallot; arrythmias, myocardial infarction, cardiomyopathy, pulmonary hypertension, and lung disease including but not limited to chronic bronchitis and emphysema.

Similarly, methods to prevent bradyarrythmia involve administration of the one or more polypeptides according to the present invention to a subject that suffer from one or more of coronary heart disease and atheroma formation, or that previously had a myocardial infarction or conduction disorder.

Similarly, methods to prevent pulmonary hypertension involve administration of the one or more polypeptides according to the present invention to a subject that suffers from one or more of chronic bronchitis, emphysema, pulmonary embolism, and intestinal pulmonary fibrosis.

Preventing stunned myocardium involves administration of the one or more polypeptides according to the present invention to a subject that suffers from cardiac ischemia.

Preventing, treating diastolic dysfunction involves administration of the one or more polypeptides according to the present invention to a subject that suffers from left ventricular hypertrophy In a further embodiment of the methods of the invention, the method is used to promote wound healing and/or reduce scar formation. In these embodiments, an "individual in need thereof" is an individual that has suffered or will suffer (for example, via a surgical procedure) a wound that may result in scar formation, or has resulted in scar formation. As used herein, the term "wound" refers broadly to injuries to the skin and subcutaneous tissue. Such wounds include, but are not limited to lacerations; burns; punctures; pressure sores; bed sores; canker sores; trauma, bites; fistulas; ulcers; lesions caused by infections; periodontal wounds; endodontic wounds; burning mouth syndrome; laparotomy wounds; surgical wounds; incisional wounds; contractures after burns; tissue fibrosis, including but not limited to idiopathic pulmonary fibrosis, hepatic fibrosis, renal fibrosis, retroperitoneal fibrosis, cystic fibrosis, blood vessel fibrosis, heart tissue fibrosis; and wounds resulting from cosmetic surgical procedures. As used herein, the phrase "reducing scar formation" means any decrease in scar formation that provides a therapeutic or cosmetic benefit to the patient. Such a therapeutic or cosmetic benefit can be achieved, for example, by decreasing the size and/or depth of a scar relative to scar formation in the absence of treatment with the methods of the invention, or by reducing the size of an existing scar. As used herein, such scars include but are not limited to keloids; hypertrophic scars; and adhesion formation between organ surfaces, including but not limited to those occurring as a result of surgery. Such methods for reducing scar formation, are clinically useful for treating all types of wounds to reduce scar formation, both for reducing initial scar formation, and for therapeutic treatment of existing scars (i.e.: cutting out the scar after its formation, treating it with the compounds of the invention, and letting the scar heal more slowly). Such wounds are as described above. As used herein, the phrase "promoting wound healing" means any increase in wound healing that provides a therapeutic or cosmetic benefit to the patient. Such a therapeutic benefit can be achieved, for example, by one or more of increasing the rate of wound healing and/or increasing the degree of wound healing relative to an untreated individual. Such wounds are as described above.

In this embodiment, it is preferred that the one or more polypeptides are disposed on or in a wound dressing or other topical administration. Such wound dressings can be any used in the art, including but not limited to films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), cellophane, and biological polymers such as those described in US patent application publication number 20030190364, published Oct. 9, 2003.

As used herein for all of the methods of the invention, an "amount effective" of the one or more polypeptides is an amount that is sufficient to provide the intended benefit of treatment. An effective amount of the polypeptides that can be employed ranges generally between about 0.01 µg/kg body weight and about 10 mg/kg body weight, preferably ranging between about 0.05 µg/kg and about 5 mg/kg body weight. However dosage levels are based on a variety of factors, including the type of injury, the age, weight, sex, medical condition of the individual, the severity of the condition, the route of administration, and the particular compound employed. Thus, the dosage regimen may vary widely, but can be determined routinely by a physician using standard methods.

The present invention may be better understood with reference to the accompanying examples that are intended for purposes of illustration only and should not be construed to limit the scope of the invention, as defined by the claims appended hereto.

EXAMPLES

Materials and Methods

Peptide Synthesis and Purification

Peptides were synthesized using standard f-moc chemistry and purified using high performance liquid chromatography (HPLC) by Cell Essentials (Boston, Mass.). Fluorescent peptides were synthesized with a fluorescein isothiocyanate (FITC) labeled on the N terminus, using β-alanine as a linker.
Cell Culture, Immunocytochemistry, and Interference Reflection Microscopy Unless otherwise stated, all reagents were purchased from Sigma, St. Louis, Mo. Swiss Albino 3T3 fibroblasts (ATCC, Manassas, Va.) were cultured in DMEM supplemented with 10% BCS, 4 mM L-glutamine and 50 µg/ml penicillin-streptomycin and maintained at 37° C., 5% $CO_2$. Cells were seeded and cultured overnight. Culture media was replaced with DMEM containing 0.5% BCS 1 hour prior to experimentation. Cells were incubated with the peptide analogues or reagent (LPA or forskolin) diluted in DMEM containing 0.5% BCS, 30 minutes at 37° C. Cells were then fixed in 4% paraformaldehyde, permeabilized in 0.25% Triton X-100, and blocked with 1% BSA solution for 1 hour. To determine α-actin cytoskeletal distribution, treated cells were incubated with Alexa 568 phalloidin (Molecular Probes, Eugene, Oreg.) in 1% BSA, 30 min. To determine focal adhesion protein localization, treated cells were incubated with primary monoclonal antibodies for α-actinin (1:100, Upstate, Charlottesville, Va.), vinculin (1:100, Sigma) or paxillin (1:100, BD Bioscience-Transduction Labs, San Jose, Calif.) in 1% BSA solution for 2 hours, rinsed in PBS and incubated 60 minutes with Cy3-goat IgG secondary antibody (Jackson ImmunoResearch, West Grove, Pa.). Slides were mounted and analyzed by confocal microscopy (Leica TCS SP2, Bannockburn, Ill.). Interference reflection microscopy was used to determine the percentage of 3T3 cells positive for focal adhesions. Cells were cultured as described above and either untreated or treated with 100 nM Hep I (thrombospondin peptide), 10 µM and 25 µM pHSP20 (phospho HSP20 peptide) or 10 µM and 25 µM sHSP20 (scrambled HSP20 peptide).
Immunoblotting 3T3 cells were lysed in a 20 mM HEPES, 15 mM EDTA, 2 mM EGTA, 1% Triton-100 solution. Proteins from cell lysate (20 µg) were separated on 15% SDS-PAGE gels and transferred to Immobilon membrane (Millipore, Billerica, Mass.). The blots were blocked in 5% milk/TBS/Tween-20 for 1 hour. The blots were then incubated with either anti-cofilin (1:1000, BD Bioscience-Transduction Labs) or phosphorylation state-specific cofilin antibody (1:2000, Chemicon, Temecula, Calif.) in TBS/milk for 1 hour at room temperature. The blots were washed 3 times (10 minutes each) in TBS/Tween-20. The cofilin and phospho-cofilin blots were placed in either goat anti-mouse or goat anti-rabbit secondary antibody (Jackson ImmunoResearch) diluted in TBS/milk (1:20,000) for 1 hour at room temperature. The blots were then washed 3 times (10 minutes each) in TBS/Tween-20. Immunoreactive protein was determined with enhanced chemiluminescence (SuperSignal West Pico, Pierce, Rockford, Ill.) exposed on X ray film (Kodak, New Haven, Conn.).
Results To determine if HSP20 mediates cyclic nucleotide-dependent stellation, phosphopeptide analogues of HSP20 (pHSP20) were synthesized that contained: 1) the amino acid sequence surrounding the phosphorylation site of HSP20 (WLRRApSAPLPGL); 2) a phosphoserine (pS); and 3) an 11 amino acid protein transduction domain from the HIV Tat protein (YGRKKRRQRRR). Control peptides contained the same sequence as the phosphopeptide analogues except with either an alanine in place of the phosphoserine (aHSP20) or a scrambled HSP20 sequence containing phosphoserine (scrHSP20, PRpSLWALGRPLSAK). Swiss 3T3 cells were treated with pHSP20 or aHSP20 (25 µM, 30 minutes), fixed, and the actin fibers stained with phalloidin. Cells that had been exposed to serum (10%) or lysophosphatidic acid (10 µM, 30 min) displayed robust stress fibers (FIG. 1A). Cells that were treated with the adenylate cyclase activator forskolin (10 µM, 30 minutes) or with pHSP20 displayed stellate morphology and disrupted stress fibers. The control peptide aHSP20 did not lead to alterations in morphology or stress fibers.

To confirm that the loss of stress fibers is associated with loss of filamentous (f-) actin and commensurate increases in globular (g-) actin, a DNase 1 inhibition assay was performed (5). Forskolin (10 µM, 30 minutes) and pHSP20 (25 µM, 30 minutes) treatment led to increases in g-actin (FIG. 1B). Thus, transduction of pHSP20 led to similar changes in actin filament dynamics and cellular morphology, as did activation of the upstream adenylate cyclase activator forskolin.

Figure 2:
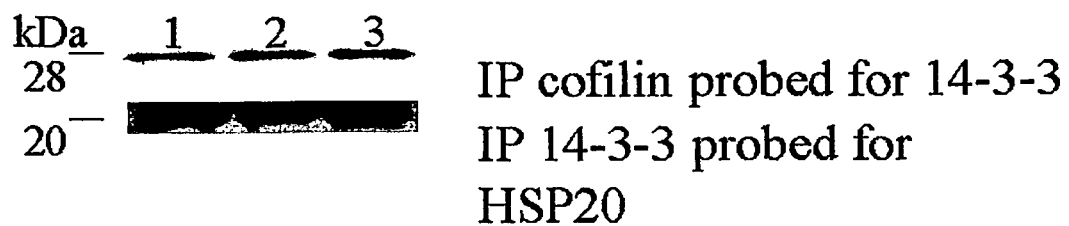
FIG. 2: 14-3-3 associates with HSP20 in porcine coronary artery immunoprecipitation. Tissue was treated as indicated and snap frozen. Resuspended protein was immunoprecipitated with cofilin (upper panel) and 14-3-3 (lower panel) and immunoblotted for 14-3-3 and HSP20, respectively.

To further verify disruption of the actin cytoskeletal network upon addition of pHSP20, the presence of focal adhesions was examined by interference reflection microscopy (6, 7). Focal adhesions are plaque-like scaffolds of both structural and signaling proteins that link the cytoskeleton to the extracellular matrix through integrin and syndecan receptors. Focal adhesions are formed in response to cell adhesion and involve signaling through Rho. These are dynamic structures that undergo disassembly and restructuring, characterized by loss of stress fibers and dispersion of vinculin, α-actinin, and paxillin, and are associated with increased cell motility. The matricellular proteins thrombospondin and tenascin-C cause focal adhesion disassembly and introduction of the intermediate cell adhesive state in a manner that requires basal PKG activity (7). Cells treated with forskolin or pHSP20 displayed a decrease in focal adhesion accumulations of α-actinin, vinculin, and paxillin (FIG. 2A-C), while cells treated with aHSP20 appeared to retain focal adhesion proteins. The pHSP20 led to disruption of focal adhesions in cultured 3T3 cells similar to the loss of focal adhesions that occurred with the hep I peptide of thrombospondin (FIG. 2D), which has been shown to signal focal adhesion disassembly in a PKG-dependent manner (7). Again, aHSP20 had no effect on focal adhesions. These data suggest that phosphorylated HSP20 might be one of the downstream effectors by which PKG mediates focal adhesion disruption.

We next examined the possible mechanisms by which pHSP20 might mediate disruption of actin filaments and focal adhesion complexes. Proteins of the ADF (actin depolymerizing family)/cofilin family are involved in actin turnover via the regulation of polymerization/depolymerization. In particular, phosphorylated cofilin is inactive; however, when dephosphorylated by the slingshot family of phosphatases, cofilin catalyzes the depolymerization of actin (8). Phosphorylated cofilin is stabilized by binding to 14-3-3 proteins (9). The 14-3-3 proteins are thought to be general biochemical regulators because they are involved with many cellular functions and have a broad range of ligands, such as receptors, kinases, phosphatases, and docking molecules (10). In addition to playing a structural role by stabilizing the activity and conformation of signaling proteins, 14-3-3 proteins also act as scaffolding proteins by interacting with and localizing phosphorlyated motifs (11). The domain surrounding the phosphorylation site in HSP20 contains a sequence (RRApSAP) similar to a putative 14-3-3 binding motif (RSXpSXP). Previous results have shown that, although highly favored, the presence of nonphosphoryated serine immediately following R is not required in this motif (12). Thus, one plausible mechanism by which pHSP20 leads to actin disruption is via competitive binding to 14-3-3 proteins resulting in release and dephosphorylation of cofilin. Consistent with this hypothesis, treatment with forskolin or with pHSP20 led to decreases in the amount of phosphorylated cofilin (FIG. 3). A similar decrease in phosphorylated cofilin has been observed with hep I treatment (13).

Taken together, these data suggest that short sequences or motifs surrounding a phosphorylation site can have profound effects on cellular biology. Since these peptides have little or no predicted tertiary structure (15), these peptide motifs are likely altering cellular function through changes in protein-protein interactions. In the case of phosphorylated HSP20, these data suggest that the motif surrounding the phosphorylation site binds to 14-3-3 proteins. Since the binding to 14-3-3 proteins is noncovalent, competitive dissociation of cofilin from 14-3-3 proteins by phosphorylated HSP20 could lead to dephosphorylation and activation of cofilin as an actin depolymerizing protein.

The transduction of peptide motifs that modulate cytoskeletal dynamics provides a framework for the development of proteomic-based therapeutics. One of the advantages of this approach is the evolutionary specificity of downstream protein targets. Receptor based modulation of signaling cascades leads to amplifying enzymatic activities. Thus, exploiting specific post-translational modifications of proteomic targets is potentially more stoichiometric and thus suitable for finer regulation of cellular processes. This approach also has advantages over gene therapy in that there are no delays in protein production or difficulties with regulating the amount of protein expression. Finally, this approach may be feasible for the treatment of specific modalities that are refractory to activation of upstream receptors or signaling cascades. For example, the vasospasm associated with subarachnoid hemorrhage occurs coincident with downregulation of the expression of HSP20 (16). These peptide analogues could be exploited for direct delivery into the CSF for the treatment of intracerebral vasospasm.

REFERENCES

1. G. J. Ramakers, W. H. Moolenaar, *Exp. Cell Res.* 245, 252 (1998).
2. A. Beall et al., *J. Biol. Chem.* 274, 11344 (1999).
3. C. R. Flynn et al., *Faseb J.* 17, 1358 (2003).
4. C. S. Heacock, J. R. Bamburg, *Anal. Biochem.* 135, 22 (1983).
5. J. E. Murphy-Ullrich, S. Gurusiddappa, W. A. Frazier, M. Hook, *J. Biol. Chem.* 268, 26784 (1993).
6. J. E. Murphy-Ullrich et al., *J. Cell. Sci.* 109, 2499 (1996).
7. R. Niwa, K. Nagata-Ohashi, M. Takeichi, K. Mizuno, T. Uemura, *Cell* 108, 233 (2002).
8. A. Gohla, G. M. Bokoch, *Curr. Biol.* 12, 1704 (2002).
9. H. Fu, R. R. Subramanian, S. C. Masters, *Annu. Rev. Pharmacol. Toxicol.* 40, 617 (2000).
10. M. B. Yaffe et al., *Cell* 91, 961 (1997).
11. S. H. Zhang, R. Kobayashi, P. R. Graves, H. Piwnica-Worms, and N. K. Tonks, *J. Biol. Chem.* 272, 27281 (1997).
12. J. E. Murphy-Ullrich, unpublished data.
13. M. P. Washburn, D. Wolters, J. R. Yates III, *Nat. Biotechnol* 19, 242 (2001).
14. S. Yellamraju, P. Komalavilas, E. J. Furnish, C. R. Flynn, C. M. Brophy, data not shown.
15. S. D. Macomson, C. M. Brophy, W. Miller, V. A. Harris, E. G. Shaver, *Neurosurgery* 51, 204 (2002).

We claim:

1. A composition comprising a polypeptide consisting of an amino acid sequence according to general formula I polypeptide consisting of an amino acid sequence according to general formula I:

$$X1\text{-}X2\text{-}X3$$

wherein X1 and X3 are independently absent or comprise a transduction domain, provided that at least one of X1 and X3 is a transduction domain; and wherein X2 is $[Z1\text{-}Z2\text{-}RRA\text{-}Z3\text{-}AP]_u$, wherein Z1 is absent or is W;

Z2 is absent or is L;

Z3 is selected from the group consisting of S, T, Y, D, E, phosphoserine analogs and phosphotyrosine analogs; and u is 1-2, wherein when u is 2, the two copies of X2 are optionally separated by a spacer.

2. A pharmaceutical composition comprising the composition of claim 1 and a pharmaceutically acceptable carrier.

* * * * *

SEQUENCE LISTING

<160> NUMBER OF SEQ ID NOS: 55

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 1

Arg Arg Ala Ser Ala Pro
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide

<400> SEQUENCE: 2

Leu Arg Arg Ala Ser Ala Pro
1               5

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Trp Leu Arg Arg Ala Ser Ala Pro
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Arg Arg Ala Thr Ala Pro
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic peptide

<400> SEQUENCE: 5

Leu Arg Arg Ala Thr Ala Pro
1               5

<210> SEQ ID NO 6
<211> LENGTH: 8
<212> TYPE: PRT
<213> ORGANISM: Artificial sequence
<220> FEATURE:
<223> OTHER INFORMATION: Synthetic peptide

<400> SEQUENCE: 6

Trp Leu Arg Arg Ala Thr Ala Pro
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide

<400> SEQUENCE: 7

Arg Arg Ala Tyr Ala Pro

```
<210> SEQ ID NO 8
<211> LENGTH: 7
<212> TYPE: PRT
<213> ORGANISM: Artificial sequence
<220> FEATURE:
<223> OTHER INFORMATION: Synthetic peptide

<400> SEQUENCE: 8

Leu Arg Arg Ala Tyr Ala Pro
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide

<400> SEQUENCE: 9

Trp Leu Arg Arg Ala Tyr Ala Pro
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Arg Arg Ala Asp Ala Pro
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic peptide

<400> SEQUENCE: 11

Leu Arg Arg Ala Asp Ala Pro
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Trp Leu Arg Arg Ala Asp Ala Pro
1               5

<210> SEQ ID NO 13
<211> LENGTH: 6
<212> TYPE: PRT
<213> ORGANISM: Artificial sequence
<220> FEATURE:
<223> OTHER INFORMATION: Synthetic peptide

<400> SEQUENCE: 13

Arg Arg Ala Glu Ala Pro
1               5
```

<210> SEQ ID NO 14
<211> LENGTH: 7
<212> TYPE: PRT
<213> ORGANISM: Artificial sequence
<220> FEATURE:
<223> OTHER INFORMATION: Synthetic peptide

<400> SEQUENCE: 14

Leu Arg Arg Ala Glu Ala Pro
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide

<400> SEQUENCE: 15

Trp Leu Arg Arg Ala Glu Ala Pro
1               5

<210> SEQ ID NO 16
<211> LENGTH: 12
<212> TYPE: PRT
<213> ORGANISM: Artificial sequence
<220> FEATURE:
<223> OTHER INFORMATION: Synthetic peptide

<400> SEQUENCE: 16

Arg Arg Ala Ser Ala Pro Arg Arg Ala Ser Ala Pro
1               5                   10

<210> SEQ ID NO 17
<211> LENGTH: 14
<212> TYPE: PRT
<213> ORGANISM: Artificial sequence
<220> FEATURE:
<223> OTHER INFORMATION: Synthetic peptide

<400> SEQUENCE: 17

Leu Arg Arg Ala Ser Ala Pro Leu Arg Arg Ala Ser Ala Pro
1               5                   10

<210> SEQ ID NO 18
<211> LENGTH: 16
<212> TYPE: PRT
<213> ORGANISM: Artificial sequence
<220> FEATURE:
<223> OTHER INFORMATION: Synthetic peptide

<400> SEQUENCE: 18

Trp Leu Arg Arg Ala Ser Ala Pro Trp Leu Arg Arg Ala Ser Ala Pro
1               5                   10                  15

<210> SEQ ID NO 19
<211> LENGTH: 12
<212> TYPE: PRT
<213> ORGANISM: Artificial sequence
<220> FEATURE:
<223> OTHER INFORMATION: Synthetic peptide

<400> SEQUENCE: 19

Arg Arg Ala Thr Ala Pro Arg Arg Ala Thr Ala Pro
1               5                   10

<210> SEQ ID NO 20

```
<211> LENGTH: 14
<212> TYPE: PRT
<213> ORGANISM: Artificial sequence
<220> FEATURE:
<223> OTHER INFORMATION: Synthetic peptide

<400> SEQUENCE: 20

Leu Arg Arg Ala Thr Ala Pro Leu Arg Arg Ala Thr Ala Pro
1               5                   10

<210> SEQ ID NO 21
<211> LENGTH: 16
<212> TYPE: PRT
<213> ORGANISM: Artificial sequence
<220> FEATURE:
<223> OTHER INFORMATION: Synthetic peptide

<400> SEQUENCE: 21

Trp Leu Arg Arg Ala Thr Ala Pro Trp Leu Arg Arg Ala Thr Ala Pro
1               5                   10                  15

<210> SEQ ID NO 22
<211> LENGTH: 12
<212> TYPE: PRT
<213> ORGANISM: Artificial sequence
<220> FEATURE:
<223> OTHER INFORMATION: Synthetic peptide

<400> SEQUENCE: 22

Arg Arg Ala Tyr Ala Pro Arg Arg Ala Tyr Ala Pro
1               5                   10

<210> SEQ ID NO 23
<211> LENGTH: 14
<212> TYPE: PRT
<213> ORGANISM: Artificial sequence
<220> FEATURE:
<223> OTHER INFORMATION: Synthetic peptide

<400> SEQUENCE: 23

Leu Arg Arg Ala Tyr Ala Pro Leu Arg Arg Ala Tyr Ala Pro
1               5                   10

<210> SEQ ID NO 24
<211> LENGTH: 16
<212> TYPE: PRT
<213> ORGANISM: Artificial sequence
<220> FEATURE:
<223> OTHER INFORMATION: Synthetic peptide

<400> SEQUENCE: 24

Trp Leu Arg Arg Ala Tyr Ala Pro Trp Leu Arg Arg Ala Tyr Ala Pro
1               5                   10                  15

<210> SEQ ID NO 25
<211> LENGTH: 12
<212> TYPE: PRT
<213> ORGANISM: Artificial sequence
<220> FEATURE:
<223> OTHER INFORMATION: Synthetic peptide

<400> SEQUENCE: 25

Arg Arg Ala Asp Ala Pro Arg Arg Ala Asp Ala Pro
1               5                   10

<210> SEQ ID NO 26
<211> LENGTH: 14
<212> TYPE: PRT
```

```
-continued

<213> ORGANISM: Artificial sequence
<220> FEATURE:
<223> OTHER INFORMATION: Synthetic peptide

<400> SEQUENCE: 26

Leu Arg Arg Ala Asp Ala Pro Leu Arg Arg Ala Asp Ala Pro
1               5                   10

<210> SEQ ID NO 27
<211> LENGTH: 16
<212> TYPE: PRT
<213> ORGANISM: Artificial sequence
<220> FEATURE:
<223> OTHER INFORMATION: Synthetic peptide

<400> SEQUENCE: 27

Trp Leu Arg Arg Ala Asp Ala Pro Trp Leu Arg Arg Ala Asp Ala Pro
1               5                   10                  15

<210> SEQ ID NO 28
<211> LENGTH: 12
<212> TYPE: PRT
<213> ORGANISM: Artificial sequence
<220> FEATURE:
<223> OTHER INFORMATION: Synthetic peptide

<400> SEQUENCE: 28

Arg Arg Ala Glu Ala Pro Arg Arg Ala Glu Ala Pro
1               5                   10

<210> SEQ ID NO 29
<211> LENGTH: 14
<212> TYPE: PRT
<213> ORGANISM: Artificial sequence
<220> FEATURE:
<223> OTHER INFORMATION: Synthetic peptide

<400> SEQUENCE: 29

Leu Arg Arg Ala Glu Ala Pro Leu Arg Arg Ala Glu Ala Pro
1               5                   10

<210> SEQ ID NO 30
<211> LENGTH: 16
<212> TYPE: PRT
<213> ORGANISM: Artificial sequence
<220> FEATURE:
<223> OTHER INFORMATION: Synthetic peptide

<400> SEQUENCE: 30

Trp Leu Arg Arg Ala Glu Ala Pro Trp Leu Arg Arg Ala Glu Ala Pro
1               5                   10                  15

<210> SEQ ID NO 31
<211> LENGTH: 14
<212> TYPE: PRT
<213> ORGANISM: Artificial sequence
<220> FEATURE:
<223> OTHER INFORMATION: Synthetic peptide

<400> SEQUENCE: 31

Arg Arg Ala Ser Ala Pro Trp Leu Arg Arg Ala Ser Ala Pro
1               5                   10

<210> SEQ ID NO 32
<211> LENGTH: 14
<212> TYPE: PRT
<213> ORGANISM: Artificial sequence
<220> FEATURE:
```

<223> OTHER INFORMATION: Synthetic peptide

<400> SEQUENCE: 32

Trp Leu Arg Arg Ala Ser Ala Pro Arg Ala Ser Ala Pro
1               5                   10

<210> SEQ ID NO 33
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(9)
<223> OTHER INFORMATION: Xaa is R or optionally absent

<400> SEQUENCE: 33

Arg Arg Arg Xaa Xaa Xaa Xaa Xaa Xaa
1               5

<210> SEQ ID NO 34
<211> LENGTH: 13
<212> TYPE: PRT
<213> ORGANISM: Artificial sequence
<220> FEATURE:
<223> OTHER INFORMATION: Synthetic peptide

<400> SEQUENCE: 34

Gly Arg Lys Lys Arg Arg Gln Arg Arg Arg Pro Pro Gln
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic peptide

<400> SEQUENCE: 35

Ala Tyr Ala Arg Ala Ala Ala Arg Gln Ala Arg Ala
1               5                   10

<210> SEQ ID NO 36
<211> LENGTH: 34
<212> TYPE: PRT
<213> ORGANISM: Artificial sequence
<220> FEATURE:
<223> OTHER INFORMATION: Synthetic peptide

<400> SEQUENCE: 36

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 37
<211> LENGTH: 27
<212> TYPE: PRT
<213> ORGANISM: Artificial sequence
<220> FEATURE:
<223> OTHER INFORMATION: Synthetic peptide

<400> SEQUENCE: 37

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 38
<211> LENGTH: 12
<212> TYPE: PRT
<213> ORGANISM: Artificial sequence
<220> FEATURE:
<223> OTHER INFORMATION: Synthetic peptide

<400> SEQUENCE: 38

Pro Leu Ser Ser Ile Phe Ser Arg Ile Gly Asp Pro
1               5                   10

<210> SEQ ID NO 39
<211> LENGTH: 16
<212> TYPE: PRT
<213> ORGANISM: Artificial sequence
<220> FEATURE:
<223> OTHER INFORMATION: Synthetic peptide

<400> SEQUENCE: 39

Ala Ala Val Ala Leu Leu Pro Ala Val Leu Leu Ala Leu Leu Ala Pro
1               5                   10                  15

<210> SEQ ID NO 40
<211> LENGTH: 12
<212> TYPE: PRT
<213> ORGANISM: Artificial sequence
<220> FEATURE:
<223> OTHER INFORMATION: Synthetic peptide

<400> SEQUENCE: 40

Ala Ala Val Leu Leu Pro Val Leu Leu Ala Ala Pro
1               5                   10

<210> SEQ ID NO 41
<211> LENGTH: 15
<212> TYPE: PRT
<213> ORGANISM: Artificial sequence
<220> FEATURE:
<223> OTHER INFORMATION: Synthetic peptide

<400> SEQUENCE: 41

Val Thr Val Leu Ala Leu Gly Ala Leu Ala Gly Val Gly Val Gly
1               5                   10                  15

<210> SEQ ID NO 42
<211> LENGTH: 21
<212> TYPE: PRT
<213> ORGANISM: Artificial sequence
<220> FEATURE:
<223> OTHER INFORMATION: Synthetic peptide

<400> SEQUENCE: 42

Gly Ala Leu Phe Leu Gly Trp Leu Gly Ala Ala Gly Ser Thr Met Gly
1               5                   10                  15

Ala Trp Ser Gln Pro
            20

<210> SEQ ID NO 43
<211> LENGTH: 27
<212> TYPE: PRT
<213> ORGANISM: Artificial sequence
<220> FEATURE:
<223> OTHER INFORMATION: Synthetic peptide

```
<400> SEQUENCE: 43

Gly Trp Thr Leu Asn Ser Ala Gly Tyr Leu Leu Gly Leu Ile Asn Leu
1               5                   10                  15

Lys Ala Leu Ala Ala Leu Ala Lys Lys Ile Leu
            20                  25

<210> SEQ ID NO 44
<211> LENGTH: 18
<212> TYPE: PRT
<213> ORGANISM: Artificial sequence
<220> FEATURE:
<223> OTHER INFORMATION: Synthetic peptide

<400> SEQUENCE: 44

Lys Leu Ala Leu Lys Leu Ala Leu Lys Ala Leu Lys Ala Ala Leu Lys
1               5                   10                  15

Leu Ala

<210> SEQ ID NO 45
<211> LENGTH: 20
<212> TYPE: PRT
<213> ORGANISM: Artificial sequence
<220> FEATURE:
<223> OTHER INFORMATION: Synthetic peptide

<400> SEQUENCE: 45

Lys Glu Thr Trp Trp Glu Thr Trp Trp Thr Glu Trp Ser Gln Pro Lys
1               5                   10                  15

Lys Lys Arg Lys
            20

<210> SEQ ID NO 46
<211> LENGTH: 16
<212> TYPE: PRT
<213> ORGANISM: Artificial sequence
<220> FEATURE:
<223> OTHER INFORMATION: Synthetic peptide

<400> SEQUENCE: 46

Lys Ala Phe Ala Lys Leu Ala Ala Arg Leu Tyr Arg Lys Ala Gly Cys
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: Synthetic peptide

<400> SEQUENCE: 47

Lys Ala Phe Ala Lys Leu Ala Ala Arg Leu Tyr Arg Ala Ala Gly Cys
1               5                   10                  15

<210> SEQ ID NO 48
<211> LENGTH: 16
<212> TYPE: PRT
<213> ORGANISM: Artificial sequence
<220> FEATURE:
<223> OTHER INFORMATION: Synthetic peptide

<400> SEQUENCE: 48

Ala Ala Phe Ala Lys Leu Ala Ala Arg Leu Tyr Arg Lys Ala Gly Cys
1               5                   10                  15

<210> SEQ ID NO 49
```

```
<211> LENGTH: 16
<212> TYPE: PRT
<213> ORGANISM: Artificial sequence
<220> FEATURE:
<223> OTHER INFORMATION: Synthetic peptide

<400> SEQUENCE: 49

Lys Ala Phe Ala Ala Leu Ala Ala Arg Leu Tyr Arg Lys Ala Gly Cys
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: Synthetic peptide

<400> SEQUENCE: 50

Lys Ala Phe Ala Lys Leu Ala Ala Gln Leu Tyr Arg Lys Ala Gly Cys
1               5                   10                  15

<210> SEQ ID NO 51
<211> LENGTH: 16
<212> TYPE: PRT
<213> ORGANISM: Artificial sequence
<220> FEATURE:
<223> OTHER INFORMATION: Synthetic peptide

<400> SEQUENCE: 51

Ala Gly Gly Gly Gly Tyr Gly Arg Lys Lys Arg Arg Gln Arg Arg Arg
1               5                   10                  15

<210> SEQ ID NO 52
<211> LENGTH: 11
<212> TYPE: PRT
<213> ORGANISM: Artificial sequence
<220> FEATURE:
<223> OTHER INFORMATION: Synthetic peptide

<400> SEQUENCE: 52

Tyr Gly Arg Lys Lys Arg Arg Gln Arg Arg
1               5                   10

<210> SEQ ID NO 53
<211> LENGTH: 11
<212> TYPE: PRT
<213> ORGANISM: Artificial sequence
<220> FEATURE:
<223> OTHER INFORMATION: Synthetic peptide

<400> SEQUENCE: 53

Tyr Ala Arg Ala Ala Ala Arg Gln Ala Arg Ala
1               5                   10

<210> SEQ ID NO 54
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is phosphorylated serine

<400> SEQUENCE: 54

Arg Arg Ala Xaa Ala Pro
1               5
```

```
<210> SEQ ID NO 55
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is phosphorylated serine
<220> FEATURE:
<221> NAME/KEY: MISC_FEATURE
<222> LOCATION: (5)..(5)
<223> OTHER INFORMATION: Xaa is any amino acid

<400> SEQUENCE: 55

Arg Ser Xaa Xaa Xaa Pro
1               5
```